United States Patent
Sakuma et al.

(10) Patent No.: US 11,547,340 B2
(45) Date of Patent: Jan. 10, 2023

(54) ANALYSIS MAP GENERATING DEVICE THAT ANALYZES A ROTATING EXCITATION WAVE IN BIOLOGICAL TISSUE

(71) Applicant: THE UNIVERSITY OF TOKYO, Tokyo (JP)

(72) Inventors: Ichiro Sakuma, Tokyo (JP); Naoki Tomii, Tokyo (JP); Hiroshi Seno, Tokyo (JP); Haruo Honjo, Nagoya (JP); Masatoshi Yamazaki, Nagoya (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 666 days.

(21) Appl. No.: 16/499,539

(22) PCT Filed: Mar. 20, 2018

(86) PCT No.: PCT/JP2018/011095
§ 371 (c)(1),
(2) Date: Sep. 30, 2019

(87) PCT Pub. No.: WO2018/180796
PCT Pub. Date: Oct. 4, 2018

(65) Prior Publication Data
US 2020/0037908 A1   Feb. 6, 2020

(30) Foreign Application Priority Data

Mar. 31, 2017   (JP) .............................. JP2017-070514

(51) Int. Cl.
*A61B 5/327*   (2021.01)
*G16H 30/40*   (2018.01)

(52) U.S. Cl.
CPC ............. *A61B 5/327* (2021.01); *G16H 30/40* (2018.01)

(58) Field of Classification Search
CPC ....... A61B 8/485; A61B 5/055; A61B 8/5223; A61B 18/1492; A61B 5/316; A61B 8/08;
(Continued)

(56) References Cited

U.S. PATENT DOCUMENTS

2015/0201905 A1\* 7/2015 Ivancevich ............ A61B 8/461
   600/438
2015/0279025 A1\* 10/2015 Waki ...................... A61B 8/463
   382/103

(Continued)

OTHER PUBLICATIONS

Umapathy, Karthikeyan et al., "Phase Mapping of Cardiac Fibrillation", Basic Science for the Clinical Electrophysiologist, Circulation Arrhythm Electrophysiol., Feb. 2010, vol. 3, Issue 1, pp. 105-114.

(Continued)

*Primary Examiner* — Golam Sorowar
(74) *Attorney, Agent, or Firm* — Oliff PLC

(57) ABSTRACT

An aspect of the present disclosure calculates a phase variance value indicating a degree of variance of a phase in a surrounding of each position in a biological tissue, based on phase values of excitation wave at respective positions in the biological tissue that acts in response to excitation caused by propagation of the excitation wave in the tissue, and generates an analysis map, based on a time series of at least part of the phase variance values at the respective positions. Since the phase variance value indicates the degree of variance of the phase in the surrounding, a position having a large degree of variance of the phase in the surrounding may be specified as a rotation center of rotating excitation wave.

7 Claims, 9 Drawing Sheets

(58) Field of Classification Search
CPC ............ A61B 2034/2051; A61B 34/20; A61B 5/287; A61B 2562/046; A61B 5/361; A61B 18/14; A61B 2017/00053; A61B 8/5207; A61B 5/0095; A61B 5/14532; A61B 8/085; A61B 8/461; A61B 5/0075; A61B 5/7207; A61B 8/14; A61B 2018/00577; A61B 2576/026; A61B 5/4312; A61B 5/7203; A61B 5/0036; A61B 8/12; A61B 8/5276; A61B 2018/00839; A61B 2560/0238; A61B 5/0035; A61B 5/0042; A61B 5/015; G01S 7/52042; G01S 7/52022; G01S 15/8915; G01S 7/52036; G01S 7/52085; G01S 15/8993; G01S 7/52046; G01S 7/52071; G01S 15/8927; G01S 15/8906; G01S 15/8922; G01S 15/8954; G01S 15/8963; G01S 15/8965; G01S 15/8977; G01S 7/52038; G01S 7/52047; G01S 7/52049; G01S 7/52074; G01S 7/52077; G01S 7/52079; G01S 13/58; G01S 13/89; G01S 15/46; G01S 15/58; G16H 50/30; G16H 30/40; G16H 50/50; G01R 33/4818; G01R 33/4833; G01R 33/5616; G01R 33/5617; G01R 33/4835; G01R 33/50; G01R 33/5601; G01R 33/5602; G01R 33/56341; G01R 33/5619; G01R 33/246; G01R 33/385; G01R 33/4828; G01R 33/54; G01R 33/5608; G01R 33/381; G01R 33/443; G01R 33/4608; G01R 33/4804

See application file for complete search history.

(56) References Cited

U.S. PATENT DOCUMENTS

2015/0302605 A1* 10/2015 Sasaki .................. G11B 27/102
600/407
2016/0213341 A1* 7/2016 Salcudean ................ A61B 6/50

OTHER PUBLICATIONS

Tomii, Naoki et al., "Detection Algorithm of Phase Singularity Using Phase Variance Analysis for Epicardial Optical Mapping Data", IEEE Transactions on Biomedical Engineering, Sep. 2016, vol. 33, No. 9, pp. 1795-1803.

Apr. 24, 2018 Search Report issued in International Patent Application No. PCT/JP2018/011095.

* cited by examiner

ANALYSIS MAP GENERATING DEVICE THAT ANALYZES A ROTATING EXCITATION WAVE IN BIOLOGICAL TISSUE

This is a national phase application of PCT/JP2018/011095 filed on Mar. 20, 2018, claiming priority to Japanese Patent Application No. JP2017-070514 filed on Mar. 31, 2017, the contents of which are incorporated herein by reference.

TECHNICAL FIELD

The present disclosure relates to an analysis map generating device and a program, and more specifically relates to an analysis map generating device configured to generate an analysis map that is used to make an analysis with regard to the rotating excitation wave in a biological tissue that acts in response to excitation caused by propagation of the excitation wave in the tissue, as well as a program that causes a computer to serve as such an analysis map generating device.

BACKGROUND

The inventors have proposed a technique of generating a phase map of the excitation wave in the heart and generating a phase variance map that indicates the degrees of variance of phase in surroundings of respective positions (respective locations) by phase variance values in a numerical value range of 0 to 1, based on the phase map (as described in Non-Patent Literature 1). The phase variance value increases with an increase in the degree of variance of the phase in the surrounding, so that a rotation center of the rotating excitation wave has a large phase variance value. Accordingly, a position (location) having the phase variance value that is larger than a reference value (for example, 0.8 or 0.9) close to a value 1 may be specified as the rotation center of the rotating excitation wave.

CITATION LIST

Non-Patent Literature

"Detection Algorithm of Phase Singularity Using Phase Variance Analysis for Epicardial Optical Mapping Data", IEEE TRANSACTIONS ON BIOMEDICAL ENGINEERING, VOL. 63, NO. 9, SEPTEMBER 2016

SUMMARY

The above proposed technique enables the rotation center of the rotating excitation wave to be specified by calculating the phase variance values in relation to the phase map of the excitation wave in the heart. The rotation center of the rotating excitation wave, however, appears, disappears and shifts with time. Accordingly, an important issue is to analyze the appearance, the disappearance and the shift of the rotation center of the rotating excitation wave with time.

A main object of an analysis map generating device of the present disclosure is to generate an analysis map that is used to make an analysis with regard to rotating excitation wave. A main object of a program of the present disclosure is to cause a computer to serve as the analysis map generating device that generates an analysis map used to make an analysis with regard to rotating excitation wave.

In order to achieve the above primary aim, the analysis map generating device and a program of the present disclosure employs the following configuration.

The present disclosure is directed to an analysis map generating device and a program. An analysis map generating device generates an analysis map used to make an analysis with regard to rotating excitation wave in a biological tissue that acts in response to excitation caused by propagation of excitation wave in the tissue. The analysis map generating device includes a phase variance value calculator configured to calculate a phase variance value indicating a degree of variance of a phase in a surrounding of each position in the biological tissue, based on phase values of the excitation wave at respective positions in the biological tissue. The analysis map generating device further includes an analysis map generator configured to generate the analysis map, based on a time series of at least part of the phase variance values at the respective positions.

The analysis map generating device according to this aspect of the present disclosure calculates the phase variance value that indicates the degree of variance of the phase in the surrounding of each position in the biological tissue, based on the phase values of the excitation wave at the respective positions in the biological tissue, and generates the analysis map, based on a time series of at least part of the phase variance values at the respective positions. The phase variance value increases with an increase in the degree of variance of the phase in the surrounding as described above. A position (location) having the phase variance value that is larger than a reference value (for example, 0.8 or 0.9) may be specified as the rotation center of the rotating excitation wave. A position (location) having the phase variance value that is not larger than the reference value but that is close to the reference value suggests that the position was a rotation center at a time prior to the present time or suggests that the position is likely to become a rotation center at a time after the present time. Accordingly, an analysis map based on a time series of at least part of the phase variance values at the respective positions in the biological tissue is an analysis map used to make an analysis with regard to the rotating excitation wave. As a result, this configuration generates an analysis map used to make an analysis with regard to the rotating excitation wave.

In the analysis map generating device according to the above aspect of the present disclosure, the analysis map generator may generate the analysis map, based on time accumulation of the phase variance values at the respective positions. The analysis map based on time accumulation of the phase variance values may be, for example, a map of time accumulation of the phase variance values or a map of time average of the phase variance values. This analysis map may be used, for example, to specify a rotation center of the rotating excitation wave or to specify a position (location) that is more likely to become a rotation center of the rotating excitation wave.

In the analysis map generating device according to another aspect of the present disclosure, the analysis map generator may generate the analysis map, based on time accumulation of phase variance values that are equal to or larger than a predetermined value, among the phase variance values at the respective positions. The analysis map based on time accumulation of the phase variance values that are equal to or larger than the predetermined value may be, for example, a map of time accumulation of only the phase variance values that are equal to or larger than the predetermined value, a map generated by time accumulation of only the phase variance values that are equal to or larger than the predetermined value and subsequent binarization by using the predetermined value, or a map of time average of the phase variance values that are equal to or larger than the predetermined value. This analysis map may be used, for example, to specify the degree of retention of the rotation center of the rotating excitation wave at a specified position (location) or to specify the tracking of the rotation center of the rotating excitation wave.

In the analysis map generating device according to another aspect of the present disclosure, the analysis map generator may generate the analysis map, based on time accumulation of binarized values obtained by binarizing the phase variance values at the respective positions by using a predetermined value. The analysis map based on time accumulation of the binarized values obtained by using the predetermined value may be, for example, a map of time accumulation of the binarized values obtained by using the predetermined value or a map generated by time accumulation of the binarized values obtained by using the predetermined value and subsequent binarization. This analysis map may be used, for example, to specify the degree of retention of the rotation center of the rotating excitation wave at a specified position (location) or to specify the tracking of the rotation center of the rotating excitation wave.

In the analysis map generating device according to another aspect of the present disclosure, the analysis map generator may generate the analysis map, based on time accumulation of phase variance values that are smaller than a predetermined value, among the phase variance values at the respective positions. The analysis map based on time accumulation of the phase variance values that are smaller than the predetermined value may be, for example, a map of time accumulation of the phase variance values that are smaller than the predetermined value or a map of time average of the phase variance values that are smaller than the predetermined value. This analysis map may be used, for example, to specify a position (location) that is more likely to become a rotation center of the rotating excitation wave or to specify a position (location) that is unlikely to become a rotation center of the rotating excitation wave.

In the analysis map generating device according to another aspect of the present disclosure, the phase variance value may be calculated according to Expression (1) given below:

[Math. 1]

$$V = 1 - \left| \frac{1}{N} \sum_{k=1}^{N} e^{j\theta_k} \right| \quad (1)$$

The analysis map generating device includes a program that causes a computer to serve as an analysis map generating device configured to generate an analysis map used to make an analysis with regard to rotating excitation wave in a biological tissue that acts in response to excitation caused by propagation of excitation wave in the tissue. The program includes a step of calculating a phase variance value indicating a degree of variance of a phase in a surrounding of each position in the biological tissue, based on phase values of the excitation wave at respective positions in the biological tissue and a step of generating the analysis map, based on a time series of at least part of the phase variance values at the respective positions.

The program according to this aspect of the present disclosure causes the computer to serve as the device of calculating the phase variance value that indicates the degree of variance of the phase in the surrounding of each position in the biological tissue, based on the phase values of the excitation wave at the respective positions in the biological tissue, and generating the analysis map, based on a time series of at least part of the phase variance values at the respective positions. The phase variance value increases with an increase in the degree of variance of the phase in the surrounding as described above. A position (location) having the phase variance value that is larger than a reference value (for example, 0.8 or 0.9) may be specified as the rotation center of the rotating excitation wave. A position (location) having the phase variance value that is not larger than the reference value but that is close to the reference value suggests that the position was a rotation center at a time prior to the present time or suggests that the position is likely to become a rotation center at a time after the present time. Accordingly, making an analysis using an analysis map based on a time series of at least part of the phase variance values at the respective positions in the biological tissue assures a more appropriate analysis of, for example, the appearance, the disappearance, and the shift of the rotation center of the rotating excitation wave with time.

DESCRIPTION OF EMBODIMENTS

Figure 1:
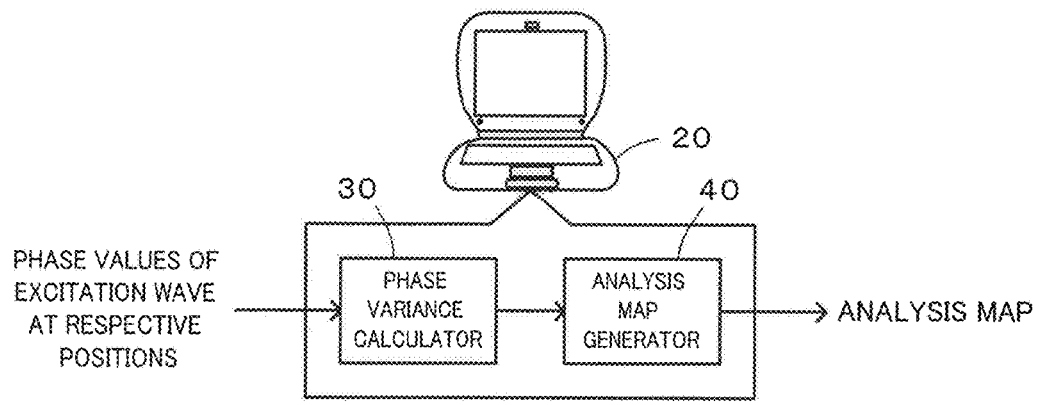
FIG. 1 is a configuration diagram illustrating the schematic configuration of an analysis map generating device 20 according to one embodiment of the present disclosure.
Figure 2:
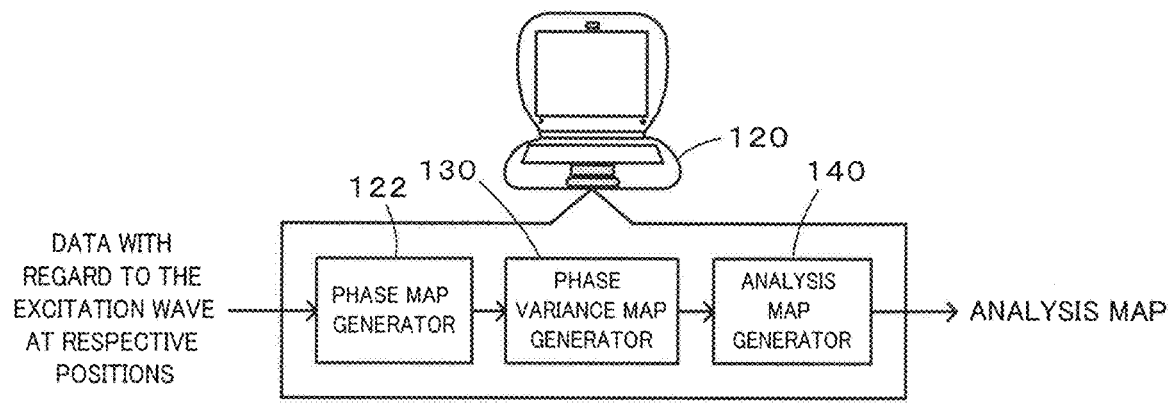
FIG. 2 is a configuration diagram illustrating the schematic configuration of an analysis map generating device 120 according to another embodiment of the present disclosure.

The following describes some aspects of the disclosure with reference to embodiments. FIG. 1 is a configuration diagram illustrating the schematic configuration of an analysis map generating device 20 according to one embodiment of the present disclosure. FIG. 2 is a configuration diagram illustrating the schematic configuration of an analysis map generating device 120 according to another embodiment that can also serve as the analysis map generating device 20 of FIG. 1.

The analysis map generating device 20 of the embodiment shown in FIG. 1 is configured by incorporating a program into a general-purpose computer, such as to cause the general-purpose computer to serve as an analysis map generator that generates an analysis map used to make an analysis with regard to rotating excitation wave in a biological tissue (for example, the heart) that acts in response to excitation caused by propagation of the excitation wave in the tissue. The analysis map generating device 20 includes a phase variance calculator 30 configured to obtain the input of the phase of the excitation wave at respective positions (locations) in the biological tissue and calculate phase variance values at the respective positions (locations); and an analysis map generator 40 configured to generate an analysis map, based on a times series of the phase variance values at the respective positions (locations) calculated by the phase variance calculator 30. The analysis map generated by the analysis map generator 40 is displayed on and output to a display connected (integrated) with the general-purpose computer.

Like the analysis map generating device 20 of the embodiment shown in FIG. 1, the analysis map generating device 120 of the embodiment shown in FIG. 2 is configured by incorporating a program into a general-purpose computer, such as to cause the general-purpose computer to serve as an analysis map generator that generates an analysis map used to make an analysis with regard to rotating excitation wave in a biological tissue that acts in response to excitation caused by propagation of the excitation wave in the tissue. The analysis map generating device 120 includes a phase map generator 122 configured to obtain the input of data with regard to the excitation wave at respective positions (locations) in the biological tissue and generate a phase map indicating the phase of the excitation wave at the respective positions (locations); a phase variance map generator 130 configured to calculate phase variance values at the respective positions (locations) in the phase map generated by the phase map generator 122 and generate a phase variance map; and an analysis map generator 140 configured to generate an analysis map, based on a time series of the phase variance values at the respective positions (locations) in the phase variance map generated by the phase variance map generator 130. The analysis map generated by the analysis map generator 140 is displayed on and output to a display connected (integrated) with the general-purpose computer.

The analysis map generating device 20 of the embodiment shown in FIG. 1 and the analysis map generating device 120 of the embodiment shown in FIG. 2 basically perform similar basic processes with a difference of whether the phase variance map is generated or not. For the purpose of illustration, the following description is based on the analysis map generating device 120 of the embodiment shown in FIG. 2 with based on the analysis map generating device 20 of the embodiment shown in FIG. 1 as needed basis.

The phase map generator 122 obtains the input of data with regard to the excitation wave at respective positions (locations) in a biological tissue and generates a phase map that indicate the phase values of the excitation wave at the respective positions at an identical time, at every predetermined time interval. For example, electric signals from sensors placed at respective positions of the heart or image data of pulsation of the heart may be used as the data with regard to the excitation wave at the respective positions (locations). The phase is expressed by a value of $-\pi$ to $\pi$ relative to the period of the excitation wave.

Figure 3:
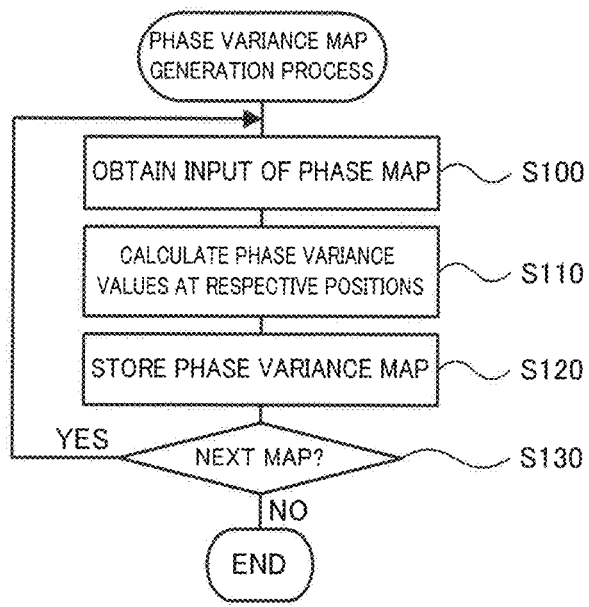
FIG. 3 is a flowchart showing one example of a phase variance map generation process.

The phase variance map generator 130 performs, for example, a phase variance map generation process shown in FIG. 3 to calculate phase variance values by using the phase values at respective positions (locations) in the phase map generated at every predetermined time interval by the phase map generator 122 and to generate a phase variance map at every predetermined time interval.

Figure 4:
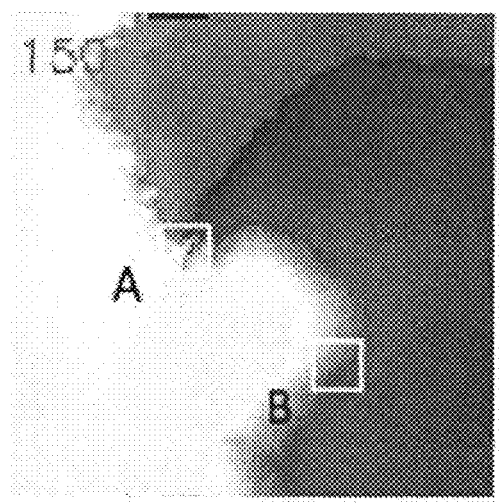
FIG. 4 is a diagram illustrating one example of a phase map indicating phase values in shading.
Figure 5:
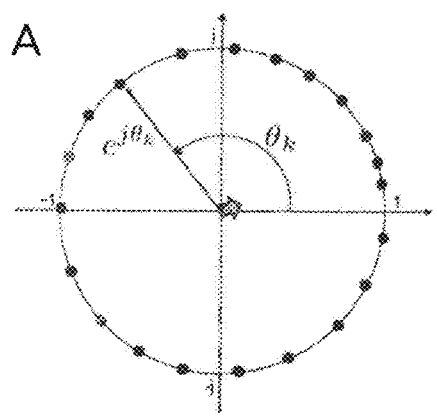
FIG. 5 is a diagram illustrating an average vector of phase values at surrounding positions of a position A shown in FIG. 4.
Figure 6:
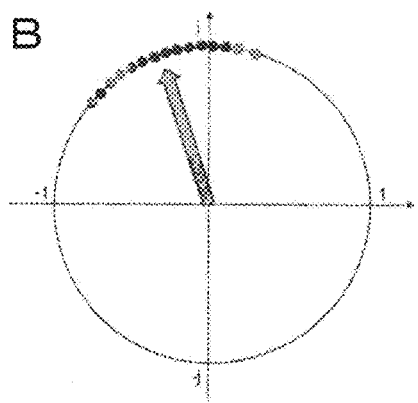
FIG. 6 is a diagram illustrating an average vector of phase values at surrounding positions of a position B shown in FIG. 4.
Figure 7:
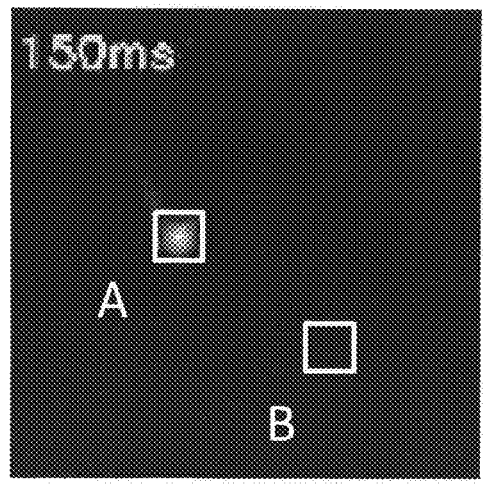
FIG. 7 is a diagram illustrating a phase variance map in relation to the phase map shown in FIG. 4.

The phase variance map generation process first obtains the input of a phase map (step S100) and calculates phase variance values at respective positions (locations) in the input phase map according to Expression (1) given below (step S110). Expression (1) subtracts a norm of an average vector of N phase values at surrounding positions of a target position, from a value 1. In Expression (1), V denotes a phase variance value, N denotes the number of the surrounding positions, and $\theta k$ denotes a phase at a position k. FIG. 4 is a diagram illustrating one example of a phase map indicating phase values in shading. FIG. 5 is a diagram illustrating an average vector of phase values at surrounding positions of a position A shown in FIG. 4. FIG. 6 is a diagram illustrating an average vector of phase values at surrounding positions of a position B shown in FIG. 4. Thick arrows in FIG. 5 and FIG. 6 respectively indicate average vectors of phase values at surrounding positions. With regard to the position A, as clearly shown in FIG. 4 and FIG. 5, the phase values at the surrounding positions are almost evenly distributed from $-\pi$ to $\pi$. Accordingly, the norm of the average vector is close to a value 0, and a phase variance value V is close to a value 1. With regard to the position B, on the other hand, as clearly shown in FIG. 4 and FIG. 6, the phase values at the surrounding positions are unevenly distributed. Accordingly, the norm of the average vector is close to the value 1, and the phase variance value V is close to the value 0. FIG. 7 illustrates a phase variance map in relation to the phase map of FIG. 4. The rotation center of the rotating excitation wave may be specified by using this phase variance map. According to the embodiment, a procedure of calculating the phase variance value V sets a window in a predetermined range with regard to each target position (open squares surrounding the positions A and B in FIG. 4 and FIG. 7) and calculates the phase variance value V from the phase values at positions in the window.

[Math. 2]

After calculating the phase variance values at the respective positions in the phase map, the phase variance map generation process stores the calculated phase variance values at the respective positions in the form of a phase variance map (step S120) and determines whether there is a next phase map (phase map after the predetermined time interval) (step S130). When there is a next phase map, the phase variance map generation process returns to step S100 to obtain the input of the phase map. When there is no next phase map, on the other hand, the phase variance map generation process is terminated.

Figure 8:
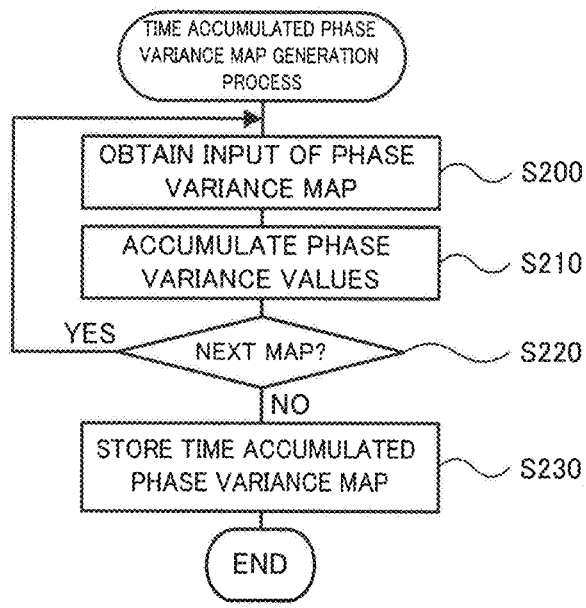
FIG. 8 is a flowchart showing one example of a time accumulated phase variance map generation process.

The analysis map generator 140 generates an analysis map, based on a time series of the phase variance values at respective positions (locations) in the phase variance map generated at every predetermined time interval by the phase variance map generator 130. For example, when the analysis map generated is a map of time accumulation of the phase variance values at respective positions (locations) in the phase variance map generated at every predetermined time interval, a time accumulated phase variance map generation process shown in FIG. 8 is performed. When the analysis map generated is a map indicating the track of the rotation center of the rotating excitation wave, a rotation center tracking map generation process shown in FIG. 9 is performed.

The time accumulated phase variance map generation process shown in FIG. 8 first obtains the input of a phase variance map (step S200), accumulates phase variance values at respective positions (locations) in the input phase variance map (step S210) and subsequently determines whether there is a next phase variance map (phase variance map after the predetermined time interval) (step S220). When there is a next phase variance map, the time accumulated phase variance map generation process returns to step S200 to obtain the input of the next phase variance map. When there is no next phase variance map, on the other hand, the time accumulated phase variance map generation process stores the accumulated values of the phase variance values at the respective positions (locations) in the form of a time accumulated phase variance map (step S230) and is then terminated.

Figure 9:
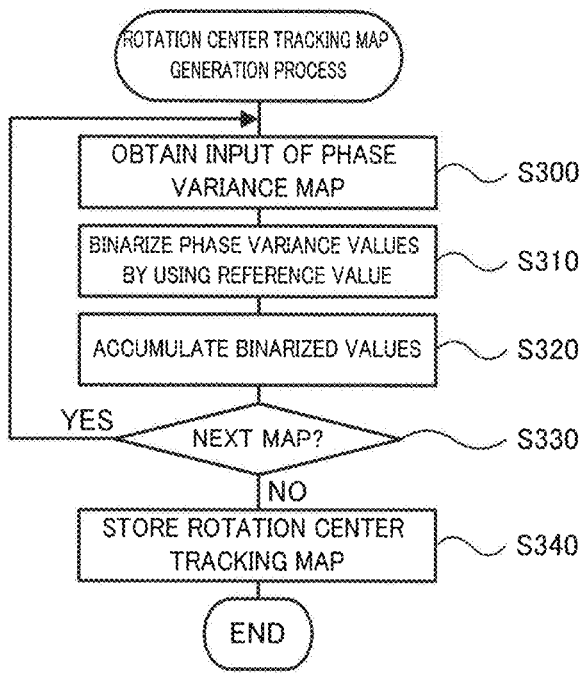
FIG. 9 is a flowchart showing one example of a rotation center tracking map generation process.

The rotation center tracking map generation process of FIG. 9 first obtains the input of a phase variance map (step S300) and determines whether a phase variance value at each position (location) is larger than a reference value (for example, 0.8 or 0.9), so as to binarize the phase variance value (step S310). This specifies the rotation center of the rotating excitation wave. The rotation center tracking map generation process subsequently accumulates the binarized values of the phase variance values at respective positions (locations) (step S320) and determines whether there is a next phase variance map (phase variance map after the predetermined time interval) (step S330). When there is a next phase variance map, the rotation center tracking map generation process returns to step S300 to obtain the input of the next phase variance map. When there is no next phase variance map, on the other hand, the rotation center tracking map generation process stores the accumulated values of the binarized values at the respective positions (locations) in the form of a rotation center tracking map (step S340) and is then terminated.

Figure 10:
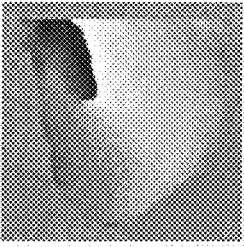
FIG. 10 is a diagram illustrating one example of phase maps, phase variance maps, and maps of binarized values obtained by binarizing phase variance values by using a threshold value at times T1 to T4 of predetermined time intervals.
Figure 11:
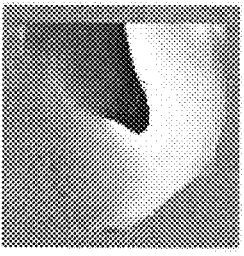
FIG. 11 is a diagram illustrating one example of the phase maps, the phase variance maps, and the maps of the binarized values obtained by binarizing the phase variance values by using the threshold value at times T5 to T8 of the predetermined time intervals.
Figure 12:
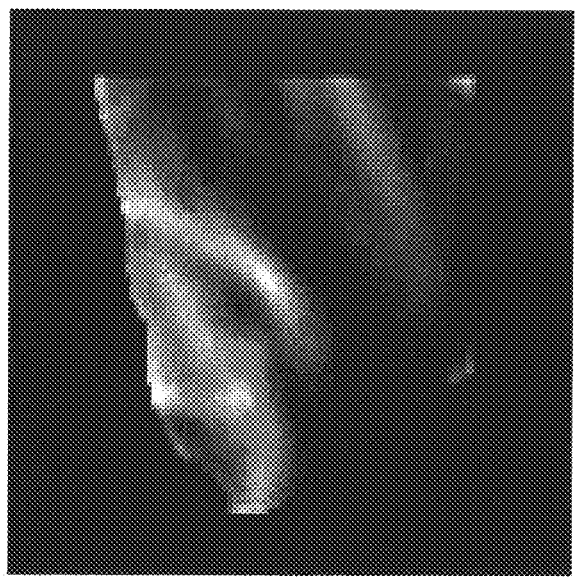
FIG. 12 is a diagram illustrating a time accumulated phase variance map in relation to the phase variance maps shown in FIGS. 10 and 11.
Figure 13:
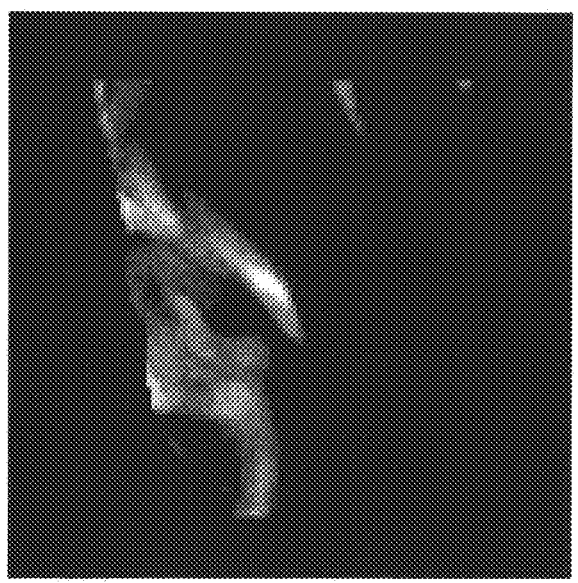
FIG. 13 is a diagram illustrating a rotation axis tracking map in relation to the maps of the binarized values obtained by binarizing the phase variance values by using the threshold value shown in FIGS. 10 and 11.

FIGS. 10 and 11 illustrate phase maps, phase variance maps and maps of binarized values obtained by binarizing phase variance values by using a reference value at respective times T1 to T8 of predetermined time intervals. FIG. 12 illustrates a time accumulated phase variance map in relation to the phase variance maps shown in FIGS. 10 and 11. FIG. 13 illustrates a rotation center tracking map in relation to the maps of the binarized values obtained by binarizing the phase variance values by using the reference value shown in FIGS. 10 and 11. In FIG. 12, the time accumulated value (degree of whiteness) of the phase variance values is expected to indicate the likelihood of the appearance of the rotation center of the rotating excitation wave. Accordingly, this map of FIG. 12 may be used to specify a position (location) that is a rotation center of the rotating excitation wave or that is likely to become a rotation center of the rotating excitation wave. In FIG. 13, the time accumulated value (degree of whiteness) of the binarized values is expected to indicate the degree of retention of the rotation center of the rotating excitation wave. The distribution of the time accumulated values of the binarized values (distribution of the white position) is expected to indicate a shift of the rotation center of the rotating excitation wave. Accordingly, this map of FIG. 13 may be used to specify the degree of retention of the rotation center of the rotating excitation wave at a specified position (location) and to specify the tracking of the rotation center of the rotating excitation wave.

Figure 14:
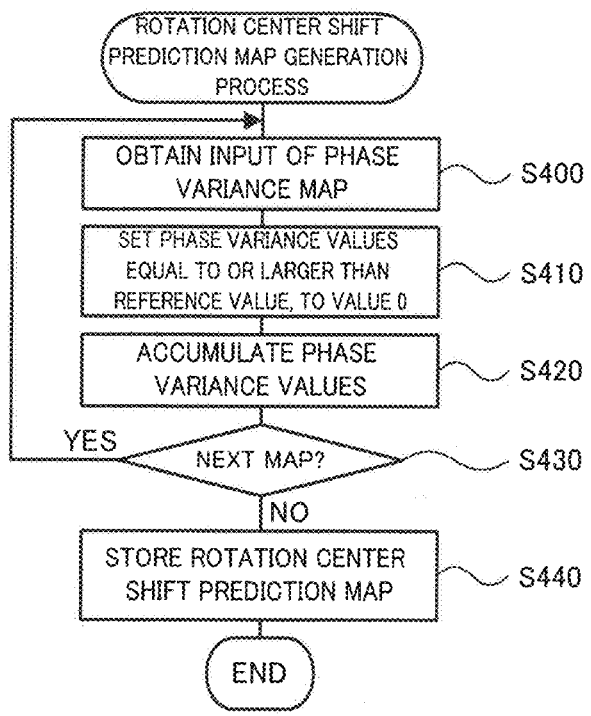
FIG. 14 is a flowchart showing one example of a rotation center shift prediction map generation process.
Figure 15:
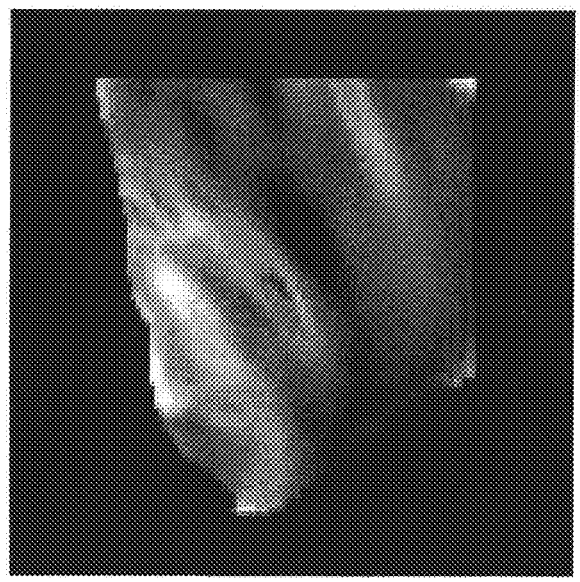
FIG. 15 is a diagram illustrating a rotation center shift prediction map in relation to the phase variance maps shown in FIGS. 10 and 11.

The analysis map generator 140 may be configured to generate a map of time accumulation of phase variance values that are smaller than a reference value (for example, 0.8 or 0.9) at respective positions (locations) in the phase variance map generated at every predetermined time interval, as a rotation center shift prediction map. In this modification, a rotation center shift prediction map generation process shown in FIG. 14 may be performed. The rotation center shift prediction map generation process first obtains the input of a phase variance map (step S400) and sets phase variance values at respective positions (locations) in the phase variance map, which are equal to or larger than a reference value (for example, 0.8 or 0.9), to a value 0 (step S410). The rotation center shift prediction map generation process subsequently accumulates the phase variance values at the respective positions (locations) (step S420) and determines whether there is a next phase variance map (phase variance map after the predetermined time interval) (step S430). When there is a next phase variance map, the rotation center shift prediction map generation process returns to step S400 to obtain the input of the next phase variance map. When there is no next phase variance map, on the other hand, the rotation center shift prediction map generation process stores the accumulated values of the phase variance values at the respective positions (locations) in the form of a rotation center shift prediction map (step S440) and is then terminated. FIG. 15 illustrates a rotation center shift prediction map in relation to the phase variance maps shown in FIGS. 10 and 11. In FIG. 15, the time accumulated value (degree of whiteness) of the phase variance values is expected to indicate the likelihood that the rotation center of the rotating excitation wave is shifted. Accordingly, this map of FIG. 15 may be used to specify a position (location) that is more likely to be a rotation center of the rotating excitation wave and to specify a position (location) that is unlikely to be a rotation center of the rotating excitation wave.

The analysis map generating device 120 of the embodiment described above calculates phase variance values at respective positions (locations) in a phase map of the excitation wave at respective positions (locations) in a biological tissue, which is generated at every predetermined time interval, so as to generate a phase variance map, and generates an analysis map, based on a time series of the phase variance values at respective positions (locations) in the phase variance map. The generated analysis map may be used for analyses of the appearance, the disappearance and the shift of the rotation center of the rotating excitation wave and for analyses of the likelihood of the appearance of the rotation center of the rotating excitation wave. As a result, the analysis map generating device 120 of the embodiment contributes to analyses of the appearance, the disappearance and the shift of the rotation center of the rotating excitation wave with time.

The analysis map generating device 120 according to the embodiment performs the time accumulated phase variance map generation process of FIG. 8 to generate a map of time accumulation of the phase variance values at respective positions (locations). A modification may generate a map of time average of the phase variance values at respective positions (locations). The map in this modification is similar to FIG. 12. The analysis map generating device 120 according to the embodiment also performs the rotation center shift prediction map generation process of FIG. 14 to generate a map of time accumulation of the phase variance values at respective positions (locations), which are smaller than the reference value. A modification may generate a map of time average of the phase variance values at respective positions (locations), which are smaller than the reference value. The map in this modification is similar to FIG. 15.

Figure 16:
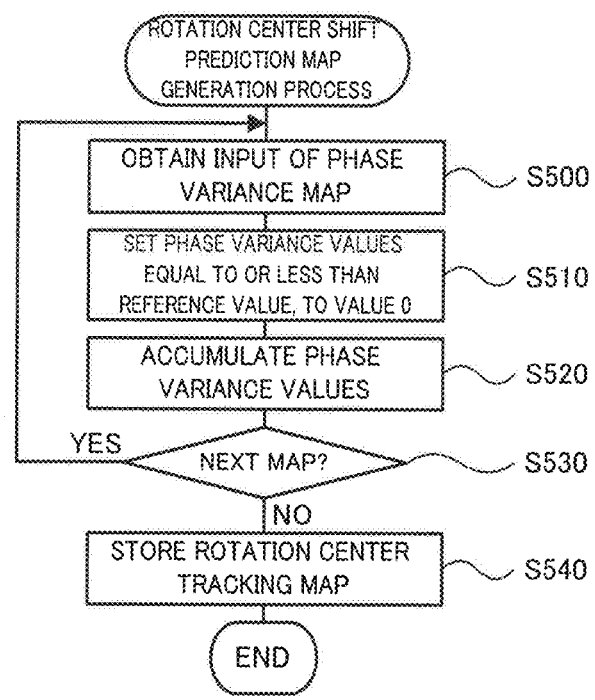
FIG. 16 is a flowchart showing one example of a rotation center tracking map generation process according to a modification.
Figure 17:
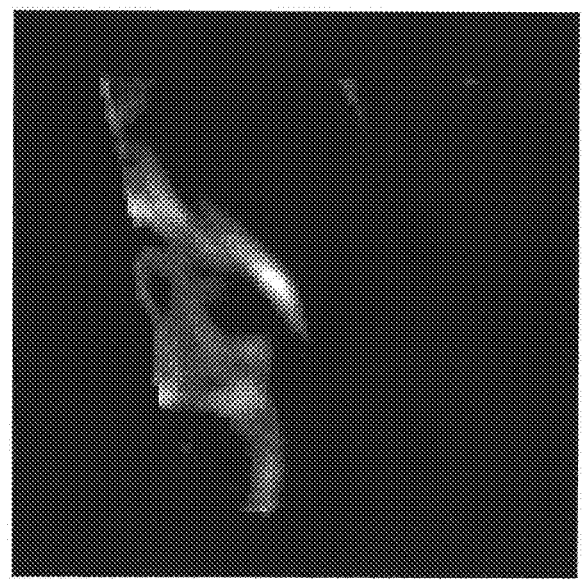
FIG. 17 is a diagram illustrating a rotation center tracking map according to the modification in relation to the phase variance maps shown in FIGS. 10 and 11.

The analysis map generating device 120 according to the embodiment generates the rotation center tracking map by accumulating the binarized values obtained by binarizing the phase variance values by using the reference value (for example, 0.8 or 0.9) at respective positions (locations). A modification may generate the rotation center tracking map by accumulating the binarized values with setting a value 1 as an upper limit. The rotation center tracking map generated in this modification is a map without shading like FIG. 13. Another modification may generate the rotation center tracking map by accumulating only phase variance values that are equal to or larger than a reference value (for example, 0.8 or 0.9), among phase variance values at respective positions (locations). A rotation center tracking map generation process shown in FIG. 16 may be performed in this modification. The rotation center tracking map generation process of FIG. 16 first obtains the input of a phase variance map (step S500) and sets phase variance values that are smaller than a reference value (for example, 0.8 or 0.9), among phase variance values at respective positions (locations), to a value 0 (step S510). The rotation center tracking map generation process subsequently accumulates the phase variance values at respective positions (locations) (step S520) and determines whether there is a next phase variance map (phase variance map after the predetermined time interval) (step S530). When there is a next phase variance map, the rotation center tracking map generation process returns to step S500 to obtain the input of the phase variance map. When there is no next phase variance map, on the other hand, the rotation center tracking map generation process stores the accumulated values of the phase variance values at the respective positions (locations) in the form of a rotation center tracking map (step S540) and is then terminated. FIG. 17 illustrates a rotation center tracking map generated by this process, in relation to the phase variance maps shown in FIGS. 10 and 11. FIG. 17 is substantially similar to FIG. 13. A modification may generate a map of time average of only phase variance values that are equal to or larger than a reference value among phase variance values at respective positions (locations), instead of generating the map of time accumulation of only the phase variance values that are equal to or larger than the reference value among the phase variance values at respective positions (locations). The map in this modification is similar to FIG. 17.

A modified procedure of generating the rotation center tracking map may generate a rotation center tracking map by counting the number of positions (locations) having phase variance values that are equal to or larger than a reference value, among respective positions (locations) in a phase variance map, which is generated at every predetermined time interval, and specifying the counted number together with such positions. This modification generates the rotation center tracking map without generating the phase variance map. Accordingly, the rotation center tracking map of this modification is generated not by the analysis map generating device 120 shown in FIG. 2 but by the analysis map generating device 20 shown in FIG. 1. Like this modification, an analysis map may be generated without generation of the phase variance map.

The aspect of the disclosure is described above with reference to the embodiment. The disclosure is, however, not limited to the above embodiment but various modifications and variations may be made to the embodiment without departing from the scope of the disclosure.

INDUSTRIAL APPLICABILITY

The technique of the disclosure is preferably applicable to the manufacturing industries of the analysis map generating device configured to generate an analysis map used to make an analysis with regard to rotating excitation wave and so on.

The invention claimed is:

1. An analysis map generating device configured to generate an analysis map used to make an analysis with regard to rotating excitation wave in a biological tissue that acts in response to excitation caused by propagation of excitation wave in the tissue, the analysis map generating device comprising:
 a processor programmed to:
  calculate a phase variance value indicating a degree of variance of a phase in a surrounding of each position in the biological tissue, based on phase values of the excitation wave at respective positions in the biological tissue; and
  generate the analysis map, based on (i) a time series of at least part of the phase variance values at the respective positions, and (ii) a determination of whether the at least part of the phase variance values are equal to or greater than a predetermined value.

2. The analysis map generating device according to claim 1,
 wherein the processor is programmed to generate the analysis map, based on time accumulation of the phase variance values at the respective positions.

3. The analysis map generating device according to claim 1,
 wherein the processor is programmed to generate the analysis map, based on time accumulation of phase variance values that are equal to or larger than the predetermined value, among the phase variance values at the respective positions.

4. The analysis map generating device according to claim 1,
 wherein the processor is programmed to generate the analysis map, based on time accumulation of binarized values obtained by binarizing the phase variance values at the respective positions by using the predetermined value.

5. The analysis map generating device according to claim 1,
wherein the processor is programmed to generate the analysis map, based on time accumulation of phase variance values that are smaller than the predetermined value, among the phase variance values at the respective positions.

6. The analysis map generating device according to claim 1,
wherein the phase variance value is calculated according to Expression (1) given below:

[Math. 1]

$$V = 1 - \left| \frac{1}{N} \sum_{k=1}^{N} e^{j\theta_k} \right|. \quad (1)$$

7. A non-transitory computer readable storage medium that stores a program that causes a computer to serve as an analysis map generating device configured to generate an analysis map used to make an analysis with regard to rotating excitation wave in a biological tissue that acts in response to excitation caused by propagation of excitation wave in the tissue, the program comprising:
  a step of calculating a phase variance value indicating a degree of variance of a phase in a surrounding of each position in the biological tissue, based on phase values of the excitation wave at respective positions in the biological tissue; and
  a step of generating the analysis map, based on (i) a time series of at least part of the phase variance values at the respective positions, and (ii) a determination of whether the at least part of the phase variance values are equal to or greater than a predetermined value.

* * * * *